(12) United States Patent
Speer et al.

(10) Patent No.: US 9,164,052 B1
(45) Date of Patent: Oct. 20, 2015

(54) INTEGRATED GAS SENSOR

(75) Inventors: Raymond Speer, Dalkey (IE); Leon Cavanagh, Loughrea (IE); Peter Smith, Summertown (GB)

(73) Assignee: Silicon Laboratories Inc., Austin, TX (US)

( * ) Notice: Subject to any disclaimer, the term of this patent is extended or adjusted under 35 U.S.C. 154(b) by 146 days.

(21) Appl. No.: 13/250,414

(22) Filed: Sep. 30, 2011

(51) Int. Cl.
G01N 27/22 (2006.01)

(52) U.S. Cl.
CPC ........................... *G01N 27/22* (2013.01)

(58) Field of Classification Search
CPC ................................ G01N 27/04; G01N 27/22
USPC .............................................. 73/31.05, 31.06
See application file for complete search history.

(56) References Cited

U.S. PATENT DOCUMENTS

| | | | |
|---|---|---|---|
| 4,057,823 A | 11/1977 | Burkhardt et al. | |
| 4,580,439 A | 4/1986 | Manaka | |
| 4,638,346 A | 1/1987 | Inami et al. | |
| 4,649,364 A | 3/1987 | Tanahashi et al. | |
| 4,793,181 A | 12/1988 | Djorup | |
| 4,831,381 A | 5/1989 | Hester | |
| 4,849,798 A | 7/1989 | Wantanabe | |
| 4,876,890 A | 10/1989 | Mercer et al. | |
| 4,931,851 A | 6/1990 | Sibbald et al. | |
| 5,041,780 A * | 8/1991 | Rippel ................. | G01R 15/207 324/117 H |
| 5,296,125 A | 3/1994 | Glass et al. | |
| 5,357,149 A | 10/1994 | Kimura | |
| 5,481,129 A | 1/1996 | DeJong et al. | |
| 5,801,428 A | 9/1998 | Felde et al. | |
| 5,878,332 A | 3/1999 | Wang et al. | |
| 6,017,775 A | 1/2000 | Igel et al. | |
| 6,051,854 A | 4/2000 | Vigna et al. | |
| 6,111,280 A | 8/2000 | Gardner et al. | |

(Continued)

FOREIGN PATENT DOCUMENTS

| JP | 358111747 | 7/1983 |
|---|---|---|
| JP | 63103957 | 10/1986 |

(Continued)

OTHER PUBLICATIONS

Silicon Labs, "C8051F99X", 25 Mips, 8 KB Flash, Ultra Low Power Capacitive Sensing MCU, May 18, 2010, 152 pgs.

(Continued)

*Primary Examiner* — Laura Martin
*Assistant Examiner* — Alex Devito
(74) *Attorney, Agent, or Firm* — Egan, Peterman & Enders LLP.

(57) ABSTRACT

An integrated circuit gas sensor system may include an integrated circuit having a bond pad layer and a dielectric layer formed after the bond pad layer. A conductor layer may be above the dielectric layer. The conductor layer may be utilized to form both gas sensor and humidity sensor conductor patterns, which may be planar. In one embodiment, the gas sensor is combined with a humidity sensor, the gas sensor and the humidity sensor covering more than 50% of the top surface of the integrated circuit. In one embodiment, the central region of the integrated circuit has a majority of its surface area utilized for the sensor structures, and in a more preferred embodiment has more than 80% of its surface area utilized for sensing structures. In one embodiment, resistive sensing may be utilized for the gas sensor and capacitive sensing may be utilized for the humidity sensor.

21 Claims, 5 Drawing Sheets

(56) References Cited

U.S. PATENT DOCUMENTS

| | | | |
|---|---|---|---|
| 6,407,449 B1 | 6/2002 | Takikawa et al. | |
| 6,417,026 B2 | 7/2002 | Gotoh et al. | |
| 6,647,782 B2 | 11/2003 | Toyoda | |
| 6,673,644 B2 | 1/2004 | Gole et al. | |
| 6,690,569 B1 | 2/2004 | Mayer et al. | |
| 6,724,612 B2 | 4/2004 | Davis et al. | |
| 6,774,613 B1 | 8/2004 | Becker et al. | |
| 7,460,958 B2 * | 12/2008 | Walsh et al. | 702/24 |
| 7,554,134 B2 | 6/2009 | Cummins | |
| 7,622,080 B2 | 11/2009 | Enquist | |
| 7,709,828 B2 | 5/2010 | Braithwaite et al. | |
| RE41,889 E | 10/2010 | Ferrari et al. | |
| 7,888,708 B2 | 2/2011 | Yazawa et al. | |
| 7,980,116 B2 | 7/2011 | Koda et al. | |
| 8,007,167 B2 | 8/2011 | Cummins | |
| 2002/0141136 A1 | 10/2002 | Toyoda et al. | |
| 2003/0010119 A1 | 1/2003 | Toyoda | |
| 2003/0010988 A1 | 1/2003 | Franson | |
| 2004/0008471 A1 | 1/2004 | Davis et al. | |
| 2005/0097941 A1 | 5/2005 | Sandvik et al. | |
| 2005/0188764 A1 | 9/2005 | Itakura et al. | |
| 2005/0199975 A1 | 9/2005 | Matubara | |
| 2008/0061323 A1 | 3/2008 | Yazawa et al. | |
| 2009/0141767 A1 | 6/2009 | Cummins | |
| 2009/0273009 A1 | 11/2009 | Cummins | |
| 2009/0324449 A1 | 12/2009 | Kira | |
| 2011/0089439 A1 | 4/2011 | Cummins | |
| 2011/0089472 A1 | 4/2011 | Cummins | |
| 2011/0098937 A1 | 4/2011 | Cummins | |
| 2011/0186995 A1 | 8/2011 | Alvarado et al. | |
| 2011/0198732 A1 | 8/2011 | Lin et al. | |
| 2011/0210446 A1 | 9/2011 | Liao et al. | |
| 2011/0226041 A1 | 9/2011 | Cummins | |

FOREIGN PATENT DOCUMENTS

| | | |
|---|---|---|
| JP | 404361149 | 12/1992 |
| WO | WO2006/090433 A1 | 8/2006 |
| WO | WO2007/097025 A1 | 8/2007 |
| WO | WO2007/099933 A1 | 9/2007 |

OTHER PUBLICATIONS

Fis, "Fis Gas Sensor, SB-500-12, for Carbon Monoxide Detection", Mar. 2006, 2 pgs.

Silicon Labs, "C8051F99X-C8051F98A", Ultra Low Power, 8-2KB Flash, Capacitive Sensing MCU, May 2011, 1 pg.

Silicon Labs, "C8051F99X Ultra Low Power Touch Sense MCUs" Printed from Internet Sep. 7, 2011, 1 pg.t.

Lemme, Elektronik, "CMOS-Sensoren gehort die Zulctutft", vol. 43, No. 24, Nov. 1994, 10 pgs.

Bousse et al., "A Process for the Combined Fabrication of Ion Sensors and CMOS Circuits", IEEE Electron Device Letters, vol. 9, No. 1, Jan. 1988, 3 pgs.

Baltes et al., "Micromachined Thermally Based CMOS Microsensors", Proceedings of the IEEE, vol. 86, No. 8, Aug. 1998, 19 pgs.

Baltes et al., "The Electronic Nose in Lilliput", Proceedings of the IEEE, vol. 35, No. 9, Sep. 1998, 4 pgs.

McCartney et al., "A Fully Integrated Sensor Interface Chip", Solid State Circuits Conference Esscirc, 1999, 4 pgs.

Cratlon, "C701 802.15.4 Zigbee Ready Wireless Sensor Module", 2004, 1 pg.

Speer et al., "Gas Sensor Having Integral Heater", U.S. Appl. No. 13/250,426, filed Sep. 30, 2011, 26 pgs.

Speer et al., "Gas Sensor Utilizing Integrated Circuit Redistribution Layer", U.S. Appl. No. 13/250,432, filed Sep. 30, 2011, 26 pgs.

Speer et al., "Systems and Methods for Packaging Integrated Circuit Gas Sensor Systems", U.S. Appl. No. 13/250,810, filed Sep. 30, 2011, 24 pgs.

Smith et al., "Methods and Materials for Forming Gas Sensor Structures", U.S. Appl. No. 13/250,831, filed Sep. 30, 2011, 27 pgs.

Smith et al.; "Gas Sensor Materials and Methods for Preparation Thereof", U.S. Appl. No. 13/250,849, filed Sep. 30, 2011, 27 pgs.

* cited by examiner

INTEGRATED GAS SENSOR

RELATED APPLICATIONS

This application is related to the following applications, all concurrently filed on the same date as the present application, including U.S. patent application Ser. No. 13/250,432, entitled "Gas Sensor Utilizing Integrated Circuit Redistribution Layer"; U.S. patent application Ser. No. 13/250,456, entitled "Gas Sensor Having Integral Heater"; U.S. patent application Ser. No. 13/250,810, entitled "Systems and Methods for Packaging Integrated Circuit Gas Sensor Systems"; U.S. patent application Ser. No. 13/250,849, entitled "Gas Sensor Materials and Methods for Preparation Thereof"; the disclosures of which are all expressly incorporated by reference herein in their entirety.

TECHNICAL FIELD OF THE INVENTION

The techniques disclosed herein relate to gas sensors, and more particularly gas sensors combined with integrated circuit technology.

BACKGROUND

A wide variety of types of gas sensors are utilized to detect gases and other ambient air conditions. For example electrochemical sensors are well known. Such sensors may include the use of a metal or plastic can which houses a liquid electrolyte having electrodes immersed in the liquid. A gas diffusion barrier allows atmosphere to ingress and make contact with a gas-sensing electrode. Infrared sensors are also well known. Infrared sensors advantageously utilized the characteristics of gases which show differing absorption spectrum at various infrared frequencies. Further, metal oxide based gas sensors, such as sensors employing precious metal (Pt, PD, AU, Ag)-activated $SnO_2$, are also known. Such sensors may utilize porous metal oxides which exhibit a shift in electrical parameters when exposed to differing gases. For example, such electrical parameters may include resistance and capacitance characteristics. Such metal oxide sensors may be housed in metal, ceramic and/or plastic can housings. Often such metal oxide based sensors utilize high operation temperatures, for example as high as 300 to 500 degrees Celsius.

The use of metal oxide based gas sensor materials in combination with integrated circuit technology to provide an integrated gas sensor has been described in U.S. Pat. No. 7,554,134, issued Jun. 30, 2009 to Cummins, and U.S. Pat. No. 8,007,167, issued Aug. 30, 2011 to Cummins, both of which are assigned to the present assignee and the disclosures of both of which are expressly incorporated by reference herein in their entirety. As described in U.S. Pat. Nos. 7,554,134 and 8,007,167 a single chip wireless gas sensor may include metal oxide sensing materials combined with a microcontroller, wireless transmit/receive circuitry, and other electrical circuits, all on a single integrated circuit. It would be desirable to provide an improved integrated circuit gas sensing platform having improved gas sensing accuracy and consistency and ease of manufacturability.

SUMMARY OF THE INVENTION

In one exemplary, non-limiting, embodiment, the gas sensor system disclosed herein advantageously provides a system in which a gas sensor is formed as part of an integrated circuit. The system may include an integrated circuit having a bond pad conductive layer formed and a dielectric layer formed after the bond pad layer. A conductor layer pattern may be formed above the dielectric layer. The conductor layer may be utilized to form a gas sensor conductor pattern and also a humidity sensor conductor pattern. The gas sensor conductors and the humidity sensor conductors may be formed in a planar manner. A planar heating element formed integrally within the gas sensor. In one embodiment, the heating element may be utilized as one electrode of the gas sensor. All such structures may be formed above the central region of an integrated circuit which contains a processor and memory. In one embodiment, the gas sensor is combined with a humidity sensor, the gas sensor and the humidity sensor covering more than 50% of the top surface of the integrated circuit. In one embodiment, the central region of the integrated circuit has a majority of its surface area utilized for the sensor structures, and in a more preferred embodiment has more than 80% of its surface area utilized for sensing structures. In this manner, a precision gas sensor may be efficiently designed, having enough capacitance and resistive regions to obtain accurate gas sensing measurements. Yet, the overall die size need not be increased because top surface area of the die may be utilized to provide the sensing structures. In one exemplary embodiment, resistive sensing may be utilized for the gas sensor and capacitive sensing may be utilized for the humidity sensor.

In another exemplary, non-limiting, embodiment a semiconductor redistribution layer (RDL) technology is utilized to form and pattern a gas sensor above an integrated circuit. An RDL insulator may be formed on the integrated circuit and an RDL conductor layer may be utilized to form the electrodes of a gas sensor above the RDL insulator. A second RDL insulator may be formed above the electrodes. A gas sensitive material may be formed within windows of the second RDL insulator. One or both of the RDL insulators may be a polyimide. A humidity sensor may be formed having electrodes which are also formed of the RDL conductive layer. Resistive sensing may be utilized for the gas sensor and capacitive sensing may be utilized for the humidity sensor. In another exemplary, non-limiting, embodiment an RDL conductor layer and dielectric layer(s) can be patterned to form multiple gas sensor sites, where differing gas sensing materials are formed on these sites and function independently of each other.

In another exemplary, non-limiting, embodiment, a planar gas sensor is provided. The sensor may include three conductive electrodes. First and second electrodes may comprise conductors having interdigitated extensions. A third electrode may be formed of a conductor that traverses between the first and second electrodes. In one embodiment, the first, second and third electrodes are formed in a planar fashion in which a common conductive layer is patterned to create the electrodes. In a gas sensing mode, the first and second conductors may be electrically connected to form one gas sensing electrode while the other gas sensing electrode is formed by the third electrode that winds between the interdigitated extensions of first electrodes. In a heating or refresh mode, two ends of the third electrode may be utilized for forming a resistive current heater. In this manner, a planar gas sensor is provided having a heating element integrally formed within the gas sensor and the heating element is also used as a sensing electrode during the sensing process.

In one exemplary embodiment, a gas sensor is provided. The gas sensor may include an integrated circuit, the integrated circuit having electrical circuits formed utilizing a semiconductor substrate. The gas sensor may further include an upper conductive layer of the integrated circuit, the upper conductive layer utilized to provide external connection to the integrated circuit, a sensor conductive layer formed after the formation of the upper conductive layer, an insulative passivation layer formed between the upper conductor layer and the sensor conductive layer and at least one sensor pattern formed in the sensor conductive layer, wherein the sensor pattern is formed in a region above at least some of the electrical circuits of the integrated circuit.

In another exemplary embodiment, a gas sensor is provided. The gas sensor may include an integrated circuit, the integrated circuit having electrical circuits formed utilizing a semiconductor substrate, a bond pad conductive layer of the integrated circuit, the bond pad conductive layer utilized to provide external connection to the integrated circuit; and a passivation layer located above at least a portion of the bond pad conductive layer. The gas sensor may further include a sensor conductive layer formed above the passivation layer, a first insulative layer formed above the sensor conductive layer, at least one region within the insulative layer within which the insulative layer is removed, a gas sensitive material located within the at least one region and at least one sensor pattern formed in the sensor conductive layer, wherein the sensor pattern is formed in a region above at least some of the electrical circuits of the integrated circuit and adjacent the gas sensitive material. The sensor pattern may be formed of electrodes for detecting electrical characteristics of the gas sensitive material.

Yet another exemplary embodiment may include a gas sensor. The gas sensor may have an integrated circuit, the integrated circuit having electrical circuits forming at least a processor and a temperature sensor, a bond pad conductive layer of the integrated circuit, the bond pad conductive layer utilized to provide external connection to the integrated circuit, and a passivation layer located above at least a portion of the bond pad conductive layer. The gas sensor may further include a sensor conductive layer formed above the passivation layer, an insulative layer formed above the sensor conductive layer, at least one region within the insulative layer within which the insulative layer is removed, and a gas sensitive material located within the at least one region. The gas sensor may further include at least two sensor patterns formed in the sensor conductive layer, wherein the sensor patterns are formed in a region above at least some of the electrical circuits of the integrated circuit and adjacent the gas sensitive material. The sensor pattern may form electrodes for detecting electrical characteristics of the gas sensitive material and detecting electrical characteristics of the insulative layer, the processor utilizing the detected electrical characteristics of the gas sensitive material, the detected electrical characteristics of the insulative layer and data from the temperature sensor to determine a gas concentration.

DETAILED DESCRIPTION OF THE INVENTION

Figure 1:
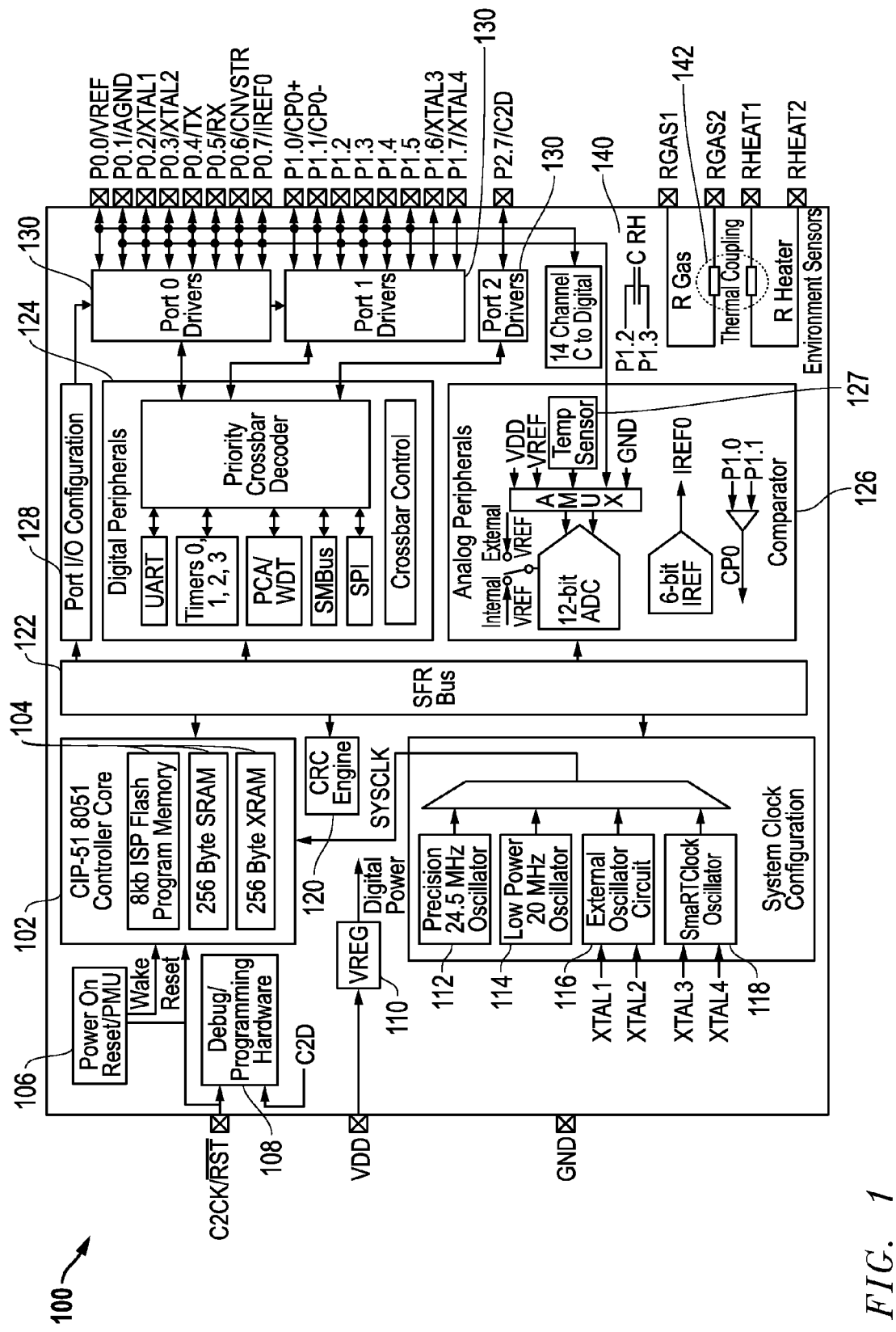
FIG. 1 is a functional electrical block diagram of one exemplary embodiment of an integrated circuit having gas sensors.

FIG. 1 illustrates an exemplary integrated circuit 100 for which the sensor techniques and concepts disclosed herein may be utilized. It will be recognized that the circuitry of integrated circuit 100 is merely exemplary and many other types of electronic circuitry may be utilized with the sensor elements disclosed herein. Thus, FIG. 1 is provided to illustrate one context within which the techniques disclosed herein may be implemented and those skilled in the art will recognize that numerous other types of integrated electronic circuits may be utilized in place of the integrated circuits shown in FIG. 1.

As shown in the exemplary embodiment of FIG. 1, the integrated circuit 100 may be a mixed signal system on a chip circuit. As shown, a processor 102 may be included, such as, for example, an 8051 compatible microcontroller. Associated memory elements 104 may also be provided. Power on/reset circuitry 106 and debug/programming circuitry 108 may also be provided. A voltage regulator 110 and a variety of system clocks 110 (a precision internal oscillator), 112 (a low power internal oscillator), 116 (an external oscillator circuit which may be coupled to an external crystal oscillator through pins XTAL1 and XTAL2), and 118 (a real time oscillator which may include an internal oscillator and can be configured for use with or without an external oscillator). A cyclic redundancy check unit 120 is also provided. A special function register bus 122 allows for special function registers to provide control and data exchange between the microcontroller core 102 and the digital peripherals 124 (crossbar control, crossbar decode, UART, timers, SMBus, SPI, programmable counter array, watchdog timer, etc.) and the analog peripherals 126 (analog to digital converter, current and voltage references, temperature sensor, comparator, etc.). The temperature sensor 127 may be, for example, a silicon bandgap temperature sensor as is well known in the art. A port I/O configuration block 128 may also be coupled to port drivers 130. The exemplary pinout shown may include a variety of Vdd, Ground, Vreference, crystal oscillator, transmit, receive, port input/output, and comparator output pins as shown.

In addition to the temperature sensor 127, other sensors may include a relative humidity sensor 140 and gas sensor 142. Other embodiments may include multiple gas sensors with specific materials and configurations selective to particular gases or airborne artifacts. As will be described in more detail below, the gas sensor 142 may be a four terminal device which includes a heater element. In the illustrative example provided herein, the relative humidity sensor 140 may have two terminals connected to shared port pinouts 1.2 and 1.3 and the gas sensor may have four pins, RGAS1, RGAS2, RHEAT1, and RHEAT2. The arrangement of the pinouts is, however, merely exemplary and other pinouts may be used. For example, dedicated pins for the humidity sensor 140 may be provided and the gas sensor could alternatively be coupled to port pins which are shared for other purposes. FIG. 1 represents a functional electrical block diagram of the various components of the integrated circuit 100. A physical layout, particularly with regard to the sensing elements will be described in more detail below.

The features disclosed in FIG. 1 provide system on a chip capability combining a microcontroller core with gas sensing technology. As shown, a microcontroller, memory, analog to digital converters, digital to analog converters, system clocks, digital ports, etc. may be combined with gas, humidity and temperature sensing technology to provide a gas sensing microcontroller unit. Though described herein with regard to an 8051 based microcontroller, it will be recognized that the sensing technology disclosed herein may be useful with any processor circuitry.

Figure 2:
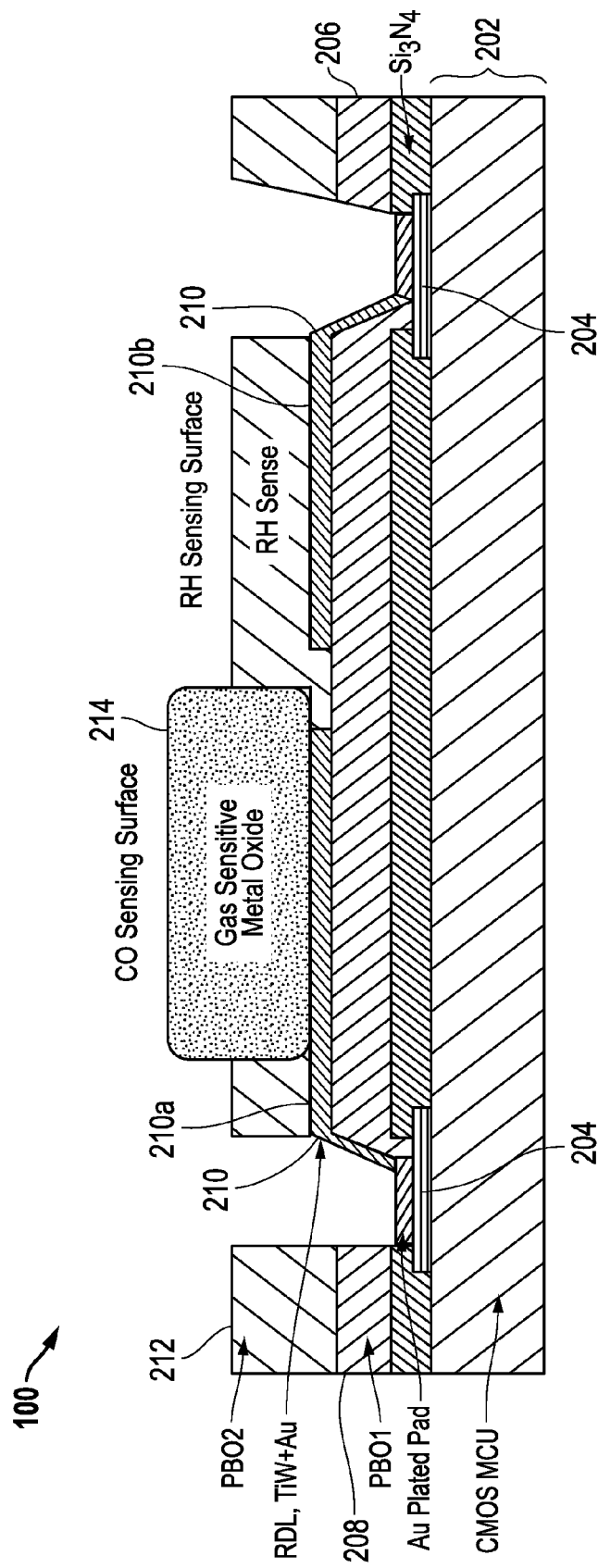
FIG. 2 is cross-section illustration of the integrated circuit of FIG. 1.

An exemplary cross section of an integrated circuit 100 is shown in FIG. 2. As shown in FIG. 2, the primary analog and digital circuitry of the various components of FIG. 1 is simplified as a CMOS structure 202. It will be recognized that CMOS structure 202 is formed through the use of many standard semiconductor layers, such as a semiconductor substrate, doped semiconductor regions, MOS transistors (such as formed through N+ and P+ doping regions and transistor gates), insulator layers, vias, planarization layers, multiple metallization layers, etc. all of which is known in the art for use in forming analog and digital circuitry in a semiconductor integrated circuit. Thus, though not shown due to size constraints, it will be recognized that the CMOS structure 202 may include millions of electrical circuit elements. The final layers of a semiconductor integrated circuitry often include bond pads and a top passivation layer. For example, as shown in FIG. 2 bond pads 204 are provided to allow external connections to the integrated circuit (such as through bond wires or solder bumps). Further, a top passivation layer 206, such as for example a silicon nitride layer, may be provided to environmentally seal and protect the CMOS structure 202.

As further shown, an additional insulative layer 208 may be formed atop the passivation layer 206. Windows may be formed in the insulative layer 208 to expose the bond pads 204. Then atop the additional insulative layer 208 an additional conductive layer 210 may be provided. The insulative layer 208 and conductive layer 210 may be formed using redistribution layer (RDL) technology known in the semiconductor processing art. Typically, RDL technology is utilized to allow the location of bond pads (usually at the outer edges or periphery of an integrated circuit) to be redistributed to other locations across an integrated circuit die, for example for solder bump placement. As described herein, RDL technology may be utilized to form and pattern a gas sensor and humidity sensor above an integrated circuit. It will be recognized that alternative technology may be utilized to form and pattern the sensor atop the integrated circuit. Insulative layer 208 may be any of a wide range of insulating materials, often polymer base and in one exemplary non-limiting example, a polyimide, and in another exemplary non-limiting example a polybenzoxazole (PBO) layer. Similar, conductive layer 210 (which may include portions 210a and 210b) may be formed of a wide range of conductive materials and in one exemplary non-limiting example, a titanium/tungsten/gold/titanium (TiW—Au—Ti) layer (though shown in FIG. 2 as TiW—Au, a top titanium layer may be added). It will be recognized that many other materials may be utilized for layers 208 and 210 as is known in the art in order to provide a mechanism to form a redistribution layer conductor atop a standard integrated circuit structure. Atop the RDL conductor layer 210 a second insulative layer 212 may be formed, in one exemplary non-limiting example, a polymer layer such as a polyimide and in another non-limiting example, a second PBO layer. As shown in FIG. 2, windows may be formed in the second RDL insulative layer 212 to expose the bond pads 204. In addition, windows may be formed in the second RDL insulative layer 212 to provide the location for a gas sensitive layer 214. As known in the art, the polyimide layers and PBO layers may be heat cured after formation. Gas sensitive layer 214 may be, in a non-limiting example, a gas sensitive metal oxide layer. Any of a wide range of gas sensitive materials may be utilized. The gas sensitive materials utilized may also depend upon the desired gas(es) being detected. For example, in one non-limiting embodiment, carbon monoxide (CO) or methane may be detected. In one non-limiting embodiment the gas sensitive material may be a tin oxide ($SnO_2$) doped with platinum and antimony such as disclosed in concurrently filed U.S. patent application Ser. No. 13/250,849, entitled "Gas Sensor Materials and Methods for Preparation Thereof" the disclosure of which is expressly incorporated by reference in its entirety. In one exemplary embodiment, the tin oxide doped with platinum and antimony may be deposited through a stencil printing process in which the gas sensitive material is incorporated in a solvent/binder carrier, as described in more detail in said U.S. patent application Ser. No. 13/250,849, entitled "Gas Sensor Materials and Methods for Preparation Thereof", the disclosure of which is expressly incorporated herein by reference in its entirety. Thus, one of the exemplary embodiments disclosed herein includes a gas sensor having electrodes formed as part of an RDL conductor layer by use of a stencil printing process. Such stencil processing may advantageously be used due to similarities to back-end integrated circuit packaging processes which utilize stencil deposition for solder paste deposition for flip chip packaging. It will be recognized that the gas sensitive layer may be formed in many other different manners, including for example but not limited to, deposition processes, ink-jet processes, droplet deposition, spin-on coating, printing processes, screen printing, stencil printing, electroplating and the like. The gas sensor material may also be deposited by spin-on coating, which covers the whole wafer surface, followed by removal of excess material for all regions except the sensor site.

According to one non-limiting embodiment of the techniques disclosed herein the RDL technology may be utilized in the formation of sensors placed atop a standard integrated circuit. As shown in FIG. 2, portions 210a of the RDL conductor and gas sensitive material 214 may be utilized for sensing a gas through exposure of the gas sensitive material to a gas containing atmosphere as will be described in more detail below. Similarly, conductor portions 210b and the second PBO layer 212 may be utilized for sensing humidity levels in the atmosphere. Thus, in the exemplary embodiment shown, the second PBO layer may be utilized for humidity sensing. However, other humidity sensitive material may be utilized in place of the PBO layer 212, such as for example polyimides. Alternatively, it will be recognized that an additional humidity sensing material may be placed in windows within the second PBO for use in humidity sensing operations.

Figure 3:
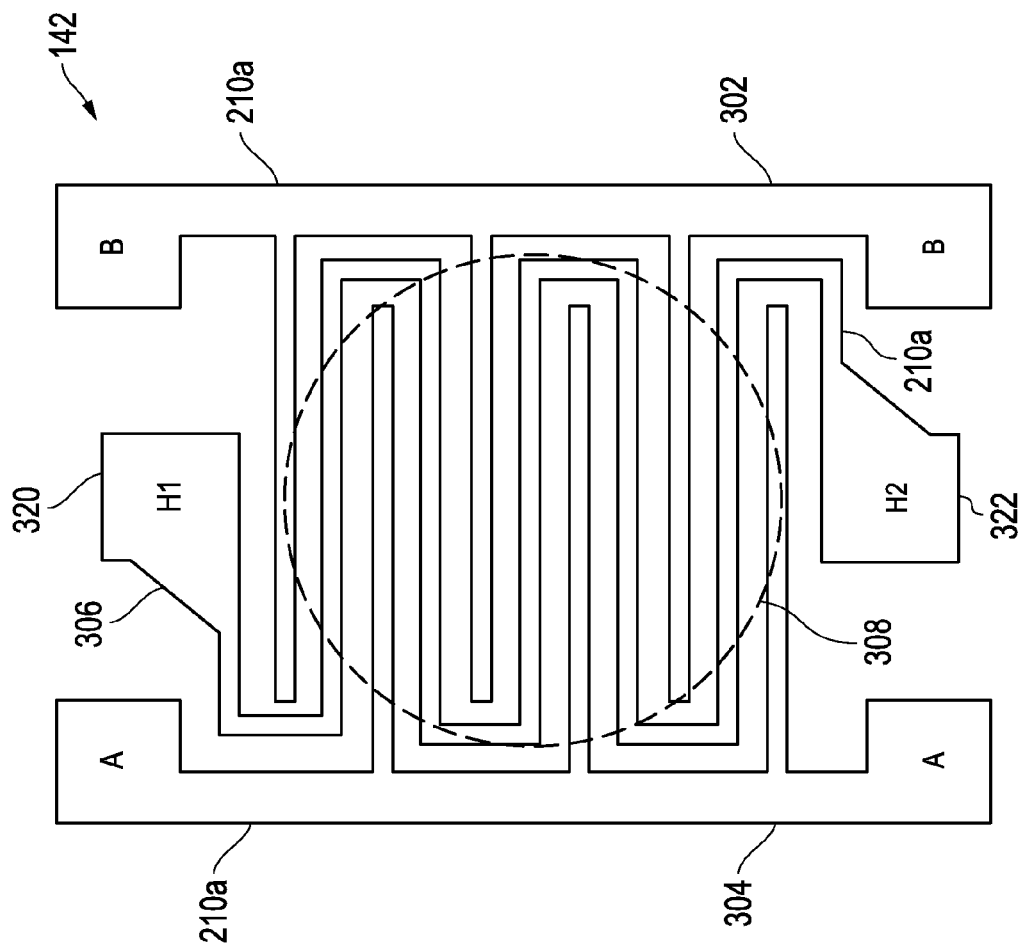
FIG. 3 is an exemplary layout of the electrodes of the gas sensor of FIG. 1.

A circuit layout of a gas sensor 142 is shown in FIG. 3. As shown in FIG. 3, a top view of the conductor pattern in the RDL conductor layer 210 for the gas sensor conductor portions 210a is provided. The conductor portions 210a are formed in the example shown in a planar fashion composed of conductor elements 302 and 304 which have interdigitated fingers or extensions as shown in FIG. 3. Conductor element 306 is formed between the elements 304 and 306 as shown. In this fashion, the conductor layer of the gas sensor may include three conductive elements all formed in substantially one plane (FIG. 3 being a top view looking down upon the plane shown in FIG. 2). Dashed line 308 shows an exemplary boundary of the window described above in the second PBO layer within which the gas sensitive material 214 may be located. In one embodiment, feature geometries of the gas sensor may be significantly larger than typical CMOS geometries. For example, features of the gas sensor may fall in the range of 50 to 500 micron feature sizes, though the techniques disclosed herein are not limited to any specific feature sizes for the gas sensor structures.

Figure 7:
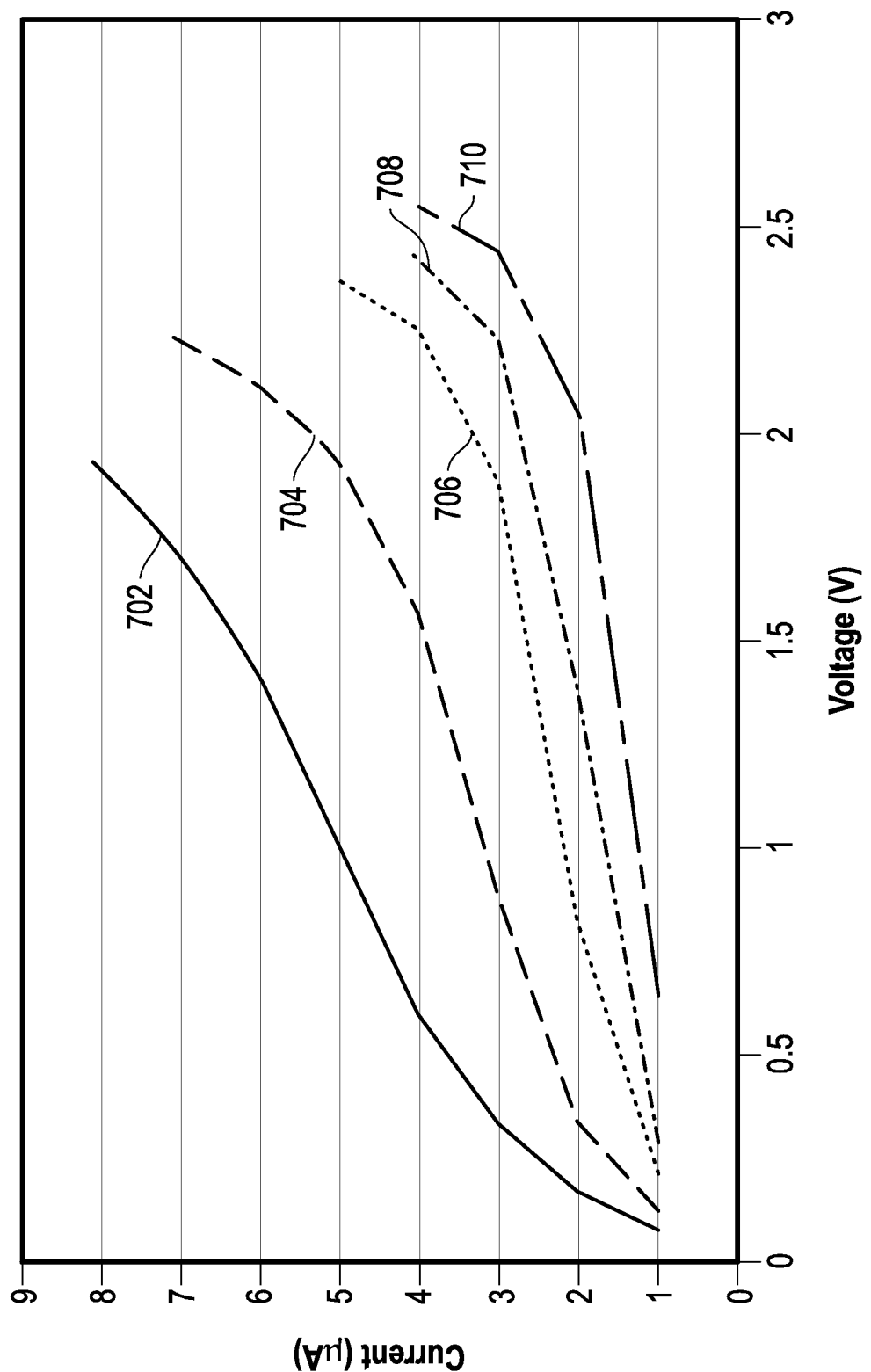
FIG. 7 is illustrates exemplary voltage vs. current plots for a metal oxide based gas sensor.

In operation, a gas sensing technique is provided in which changes in the resistivity of the gas sensitive material are detected through the use of electrical measurements at electrodes. The gas sensitive material is located over and between the electrodes and provides a variation in resistance as the amount of gas that the gas sensitive material is exposed to varies. FIG. 7 shows a plot of the sensor voltage-current characteristics at different levels of gas exposure. In one embodiment, the gas sensor 142 includes a heater element. A heater element may provide a variety of advantageous which may optionally be utilized during the gas sensing process. By heating the gas sensitive material contaminates may be removed from the gas sensitive material. In addition, if the gas sensitive material becomes saturated with the gas that is being detected, the heating element may be used to remove the gas being detected from the gas sensitive material. In one embodiment, the heater may be operated at a regular interval (for example once a day) in order to refresh the gas sensitive material. The heater may be utilized to create a thermal pulse in the gas sensitive material in the range of approximately 100 to 300 degrees Celsius. Such temperatures are merely illustrative embodiments and other heating temperatures may be utilized to refresh the gas sensitive material. The sensor design as shown in FIG. 2 is particularly well suited for such heating because the PBO layer 208 is a relatively good thermal insulator, with a thermal conductance of approximately 0.5 W/(m K), thus limiting the heat dissipation through the rest of the integrated circuit. Alternative materials with even more thermal insulation properties may advantageously may also provide even better thermal insulation.

Thus, heating effects from the heating element may efficiently impact the gas sensitive material as one side of the heater element is in direct contact with the gas sensitive material while a relatively good thermal insulator is on the other side of the heater element. Further, as the heater element is within the same planar conductor layer as the gas sensor conductor portions and winds through such other gas sensor conductor portions, close proximity is maintained to the other structures of the gas sensor and the relevant gas sensing material. Further depending upon the gases being detected, the gas concentration vs. electrical characteristics may be dependent upon temperature. Thus, the heater element may be utilized to provide a controlled operating temperature or provide variations in temperature for obtaining measurements at differing temperatures. In addition, heating of the gas sensitive material may be used to accelerate the sensor response time in speed critical applications. Thus, there are different detection modes in which the heater may be operated or not in addition to the refresh mode. In one detection sense mode the ambient temperatures conditions may be utilized to detect gases without applying addition heat from the heater. Often such ambient conditions may range from 0 to 100 degrees Celsius. In another detection sense mode, the gas sensor may be heated during the gas detection measurements, for example between 100 to 275 degrees Celsius (often limited by the heat limits of the RDL layers utilized). In this heating mode of detection the kinetics of the reactions in the gas sensitive materials may provide improved performance with regard to the detection response and recovery and also minimize high humidity effects.

Figure 4:
FIG. 4 is a functional electrical block diagram of the gas sensor in a refresh mode.
Figure 5:
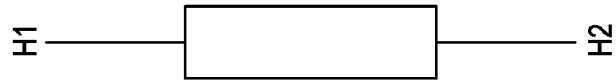
FIG. 5 is a function electrical block diagram of the gas sensor in a gas sense mode.

The gas sensor layout shown in FIG. 2 provides an advantageous design incorporating both the heater and sensing electrodes in a planar fashion. As shown in FIG. 3, four electrodes are provided: electrode A formed by conductive element 304, electrode B formed by conductive element 302, electrode H1 at one end 320 of conductive element 306 and electrode H2 formed at the other end 322 of conductive element 306. In operation, the conductive element 306 operates as a heater element when current is passed between electrode H1 and H2 to provide resistive heating. FIG. 4 illustrates an electrical schematic of the use of the electrodes H1 and H2 when the heater element is being utilized, such as for example in a refresh mode. When heating, in one embodiment the electrodes A and B may be floating in a tri-state status. When gas measurements are desired, measurements may be obtained by electrically connecting electrodes A and B. Electrodes A and B may be selectively coupled together just in the sense mode or alternatively may be always coupled together. Resistance measurements may then be detected between the conductive element 306 (which has electrodes 320 and 322 at either end) and the conductive elements 302 and 304 (302 and 304 being electrically tied together). FIG. 5 illustrates an electrical schematic of the electrodes utilized in a gas sensing mode. The gas sensitive material 214 which is located between the conductive elements 302, 304 and 306 within the window region 308 will provide a differing electrical measurement depending upon the concentration of gas that the gas sensitive material is exposed to.

Thus the planar interdigitated fingers of two separate conductive elements may be utilized to form one gas sensing electrode while the other gas sensing electrode is formed by yet a third conductive element that winds between the interdigitated fingers of first two conductive elements. Moreover, because the two ends of the third conductive element may be utilized for forming a resistive current heater, the heater element may be placed in close proximity to the sensing material and electrodes, improving power efficiency, heating control, heating accuracy and heating speed. In this manner, a planar gas sensor is provided having a heating element integrally formed within the gas sensor and which is also used as a sensing electrode during the sensing process.

The humidity sensor may utilize a variety of humidity sensing techniques and may be formed in a variety of manners. In one exemplary approach, a pair of separated conductors is formed in the portion 210b of the RDL conductor 210. These separate conductors may comprise interdigitated fingers or extensions somewhat similar to the arrangements of conductors 304 and 302 shown in FIG. 2. The second PBO layer 212 may extend down between the two conductors and over the two conductors. The capacitance between the two conductors may change as moisture ingresses into the PBO layer 212. Thus, capacitance variations may be utilized to reflect variations in the relative humidity. Capacitive humidity sensing techniques may include, for example, the techniques described in U.S. Pat. No. 8,007,167 to Cummins, the disclosure of which is incorporated herein by reference in its entirety. Thus, a planar capacitive humidity sensor may be formed utilizing a RDL conductor layer with an overlaying humidity sensitive dielectric layer, such as shown by RDL conductive layer 210b and PBO layer 212 of FIG. 2.

Though described herein with respect to resistive sensing for gas detection and capacitive sensing for humidity detection, other approaches may be utilized while still obtaining the benefits of the techniques described herein. For example depending upon the sensing materials used, resistive sensing may be utilized for humidity detection and capacitive sensing for gas sensing. Alternatively, both sensors could be resistive or both sensors could be capacitive. Further, gas sensing could be accomplished by a combination of both resistive and capacitive techniques and humidity sensing could be accomplished by a combination of both resistive and capacitive techniques. Thus, it will be recognized that different features and embodiments of the concepts disclosed herein may be utilized in a variety of manners, and the disclosure provided herein is not limited to the particular techniques illustrated. Further, though described herein with regard to two sensors RDL sensors it will be recognized that three or more sensors may be formed by utilizing the RDL techniques described herein. Moreover, each sensor may utilize a differing gas sensitive material or some or all may utilize the same material as the techniques described herein are not limited to the particularly exemplary embodiment described herein.

Figure 6:
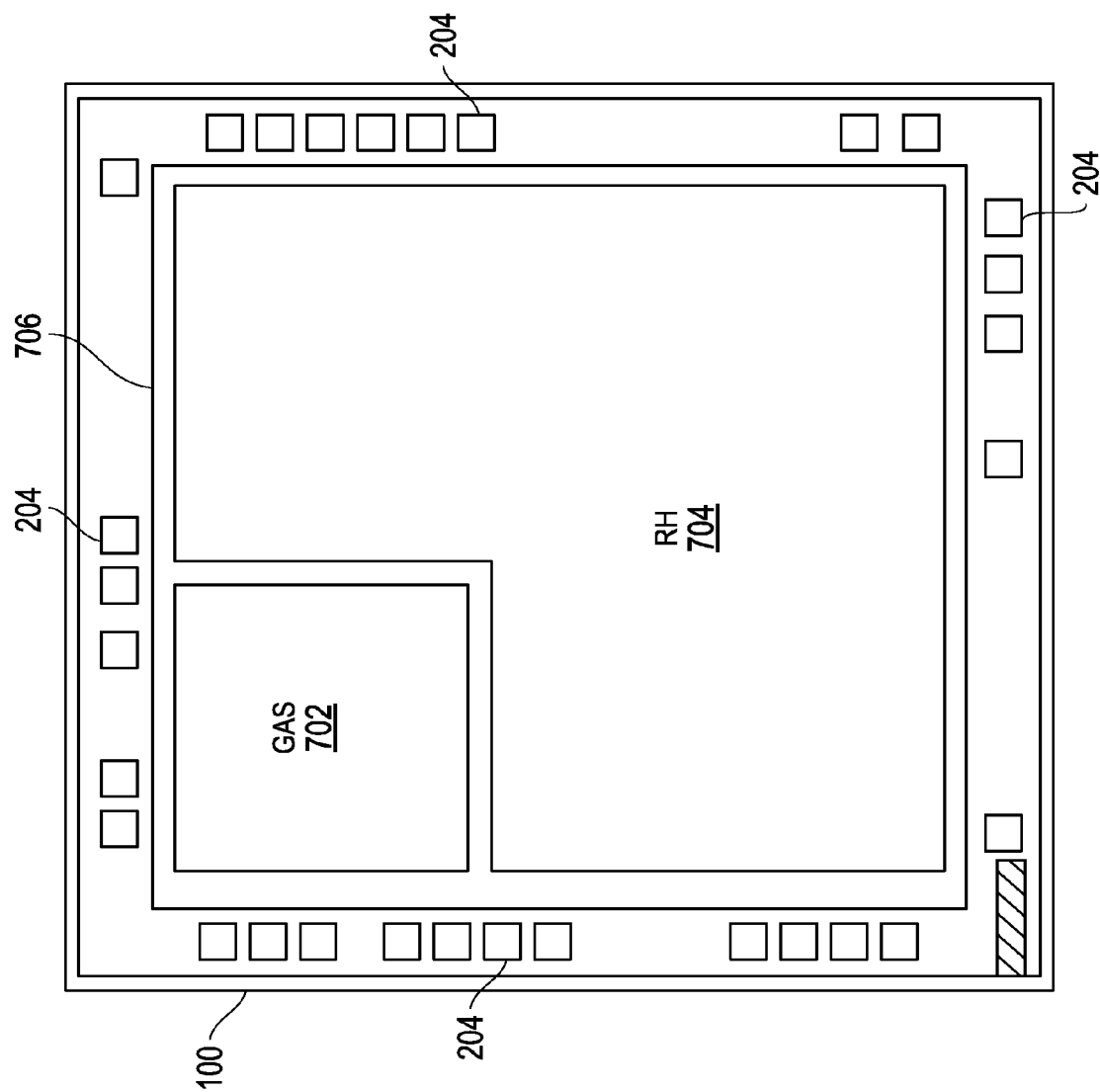
FIG. 6 is an exemplary top plan view of the integrated circuit of FIG. 1.

As shown in FIG. 2, in one embodiment the sensing structures may be located above a large portion of the integrated circuit. As shown in FIG. 6, a top view of an exemplary integrated circuit is shown. In FIG. 6 an integrated circuit 100 is provided with bond pads 204 around the periphery of the die. In the center portion of the integrated circuit the gas sensor structure and relative humidity structures may occupy a substantial majority of the upper surface central area of the integrated circuit. Thus, gas sensor 142 may be formed with RDL structures occupying the region 702 of FIG. 7. Similarly, the humidity sensor 140 may be formed with RDL structures occupying the region 704 of FIG. 7. In one exemplary embodiment, an integrated circuit may be approximately 1.56 mm by 1.68 mm in size and have a central region bounded by line 706. The central region of the integrated circuit has a majority of its surface area utilized for the sensor structures, and in a more preferred embodiment has more than 80% of its surface area utilized for sensing structures. In this manner, a precision gas sensor may be efficiently designed, having enough capacitance and resistive sensitive regions to obtain accurate gas sensing measurements. Yet, the overall die size need not be increased because top surface area of the die may be utilized via RDL technology to provide the sensing structures.

One advantage of the techniques disclosed herein (though the present techniques are not required to utilize such advantage) is that the CMOS structure 202 may be any of a wide variety of types of semiconductor integrated circuits and is not limited to microcontroller. Thus, any integrated circuit in which the use of a gas sensor may be desired could be used as the base circuitry for the sensing techniques disclosed herein. Thus, the techniques disclosed herein can be added to a wide variety of semiconductor process flows, merely through the addition of a redistribution layer and gas sensing layer configured in a manner as described herein. Therefore, advantageous costs, layout, and integration benefits may be obtained.

FIG. 7 illustrates exemplary data gas concentration data which may be obtained from a structure such as shown in FIG. 3. The data displayed in FIG. 7 relates to a sensor utilizing a metal oxide sensor material ($SnO_2$ doped with platinum and antimony) for detection of carbon monoxide (CO). More particularly, the data of FIG. 7 displays the voltage (v) vs. current (uA) plots for a sensor exposed to differing gas concentrations having a thirty second settling time. Plot 702 is the plot for 0 ppm of CO, Plot 704 is the plot for 30 ppm of CO, Plot 706 is the plot for 50 ppm of CO, Plot 708 is the plot for 15 0 ppm of CO, and Plot 710 is the plot for 300 ppm of CO.

In making gas detection measurements, the system described herein may also utilize the detected levels of relative humidity and temperature in order to provide a more accurate measurement of a gas concentration as the electrical characteristics of the gas sensitive materials may also be a function of temperature and relative humidity. Thus, sensors measuring temperature, gas concentration and humidity may be utilized together to provide a more accurate determination of the concentration of a particular gas. The gas sensor integrated circuit 100 of FIG. 1 is particularly well suited for such analysis because of the presence of a microcontroller, memory, analog to digital converter, digital to analog converter, temperature sensor, humidity sensor and gas sensor all on a single integrated circuit. The microcontroller and non-volatile memory may provide lookup tables, correlation tables, mathematical algorithms and the like for processing all the collected data together in order to provide a more accurate gas concentration reading. In operation, data collected by the various on chip sensors may be converted from analog levels to digital with the analog to digital converter. The digital data may then be provided to the microcontroller to perform calculations to determine a gas concentration from the sensed measurements. The microcontroller may then provide a digital output at an output pin of the integrated circuit to provide the detected concentration to a user.

As shown in FIG. 1, the electrodes of the capacitive humidity sensor 140 are directly connected to the integrated circuit data I/O pins P1.2 and P1.3 (such pins are designated for illustrative purposes and other I/O pins may be utilized in accordance with the circuit design in which the sensors are utilized with). Such connection may be made for example by connecting the capacitive sensor electrodes formed in the RDL conductive layer to the bond pads for the specified I/O pins. In the exemplary embodiment of FIG. 1, the gas sensor 142 electrodes RGAS1, RGAS2, RHEAT1, and RHEAT2 are not connected directly to the data I/O pins of the integrated circuit 100 but rather the electrodes are provided separate pinouts. Thus, wire bonding, solder bumps, etc. may in such an embodiment be provided directly to RDL bond sites for RGAS1, RGAS2, RHEAT1, and RHEAT2 pins. It will be recognized that such techniques are purely exemplary and other pin out techniques may be utilized. In operation, these gas sensor electrodes may be coupled to the other I/O pins of the integrated circuit through off chip connections such as through a circuit board to which the integrated circuit is mounted so that the microcontroller may still drive the electrodes and record the data at the electrodes. By providing separate gas sensor electrodes, external components may be used to bias the heating and gas sensing operations, thereby relieving power delivery and dissipation demands of the integrated circuit. Alternatively, the gas sensor electrodes could be directly connected on chip to port I/O pins of the integrated circuit through the RDL layer and all currents and voltages to the gas sensor could be provided from the integrated circuit.

The integrated circuit of FIG. 1 may be packaged in any of a wide variety of semiconductor packages and the techniques described herein are not limited to a particular type of integrated circuit package. Rather, it is only desirable that the gas sensing material and humidity sensing material formed in the RDL layers be exposed to the atmosphere that is being measured. One exemplary embodiment of a suitable package is shown in concurrently filed U.S. patent application Ser. No. 13/250,810, entitled "Systems and Methods for Packaging Integrated Circuit Gas Sensor Systems," the disclosure of which is incorporated herein by reference.

Thus, a system is disclosed in which an integrated circuit having a bond pad conductive layer is formed and a dielectric layer formed after the bond pad layer. A redistribution layer conductor pattern may be formed above the dielectric layer. This conductor may be utilized to form a gas sensor conductor pattern. The gas sensor conductor may be formed in a manner that creates a planar gas sensor structure. The planar structure may have a planar heating element formed integrally within the gas sensor. In one embodiment, the heating element may be utilized as one electrode of the gas sensor. The gas sensor conductor layer may be formed above an RDL PBO dielectric layer and may further have a second RDL PBO conductive layer located above the gas sensor conductor layer. All of such structures may be formed above the central region of an integrated circuit which contains a processor and memory. In one embodiment, the gas sensor is combined with a humidity sensor, the gas sensor and the humidity sensor covering more than 50% of the top surface of the portion of the integrated circuit between the bond pads of the integrated circuit.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures. For example, equivalent elements may be substituted for those illustrated and described herein and certain features of the invention may be utilized independently of the use of other features, all as would be apparent to one skilled in the art after having the benefit of this description of the invention.

The invention claimed is:

1. A gas sensor comprising:
an the integrated circuit, the integrated circuit comprising:
electrical circuits formed utilizing a semiconductor substrate;
an external connection layer configured to provide external connection location for the integrated circuit;
a sensor conductive layer formed above at least a portion of the external connection layer;
an insulative passivation layer formed between the external connection layer and the sensor conductive layer; and
at least one sensor pattern formed in the sensor conductive layer, wherein the sensor pattern is formed in a region above at least some of the electrical circuits of the integrated circuit.

2. The gas sensor of claim 1, wherein the external connection layer is a bond pad layer.

3. The gas sensor of claim 1, wherein the external connection layer is configured to be coupled to either bond wires or solder bumps or both.

4. The gas sensor of claim 1, wherein the sensor conductive layer is planar within the region where the at least one sensor pattern is formed.

5. The gas sensor of claim 1, wherein the sensor conductive layer forms a portion of a resistive sensor.

6. The gas sensor of claim 5 wherein the sensor conductive layer further forms a portion of a capacitive sensor.

7. The gas sensor of claim 6, wherein the resistive sensor and the capacitive sensor together occupy more than a majority of the top surface of the integrated circuit.

8. The gas sensor of claim 7, wherein the resistive sensor and the capacitive sensor together occupy at least 80% of the top surface of a central region of the integrated circuit.

9. The gas sensor of claim 1, wherein the sensor conductive layer forms a capacitive sensor.

10. The gas sensor of claim 1, wherein the integrated circuit comprises a processor.

11. The gas sensor of claim 10, wherein the integrated circuit further comprises a temperature sensor.

12. The gas sensor of claim 11, wherein the sensor conductive layer forms both a resistive sensor and a capacitive sensor, the processor processing data from the temperature sensor, resistive sensor and capacitive sensor to determine a gas concentration.

13. A gas sensor comprising:
an the integrated circuit, the integrated circuit comprising:
electrical circuits formed utilizing a semiconductor substrate;
a bond pad conductive layer of the integrated circuit, the bond pad conductive layer configured to provide an external connection location for the integrated circuit;
a passivation layer located above at least a portion of the bond pad conductive layer;
a sensor conductive layer formed above the passivation layer;
a first insulative layer formed above the sensor conductive layer;
at least one region within the insulative layer within which the insulative layer is removed;
a gas sensitive material located within the at least one region;
at least one sensor pattern formed in the sensor conductive layer, wherein the sensor pattern is formed in a region above at least some of the electrical circuits of the integrated circuit and adjacent the gas sensitive material,
the sensor pattern forming electrodes for detecting electrical characteristics of the gas sensitive material.

14. The gas sensor of claim 13, further comprising a second insulative layer, the second insulative layer being located between the passivation layer and the sensor conductive layer.

15. The gas sensor of claim 13, wherein the sensor pattern forms electrodes for a gas sensor and a relative humidity sensor.

16. The gas sensor of claim 13, wherein the gas sensor utilizes the gas sensitive material to detect electrical changes in the gas sensitive material that result from exposure to a gas and the humidity sensor utilizes the first insulative layer to detect electrical changes in the first insulative layer that result from exposure to humidity.

17. The gas sensor of claim 13, wherein the integrated circuit comprises a processor.

18. The gas sensor of claim 17, wherein the integrated circuit further comprises a temperature sensor.

19. The gas sensor of claim 18, wherein the sensor conductive layer forms at least one of a resistive sensor and a capacitive sensor, the processor processing data from the temperature sensor, resistive sensor and capacitive sensor to determine a gas concentration.

20. A gas sensor comprising:
an integrated circuit comprising:
electrical circuits formed at least in part in a semiconductor substrate, the electrical circuits including at least a processor and a temperature sensor;
a bond pad conductive layer of the integrated circuit, the bond pad conductive layer configured to provide an external connection location for the integrated circuit;
a passivation layer located above at least a portion of the bond pad conductive layer;
a sensor conductive layer formed above the passivation layer;
an insulative layer formed above the sensor conductive layer;
at least one region within the insulative layer within which the insulative layer is removed;
a gas sensitive material located within the at least one region;

at least two sensor patterns formed in the sensor conductive layer, wherein the sensor patterns are formed in a region above at least some of the electrical circuits of the integrated circuit and adjacent the gas sensitive material, the sensor pattern forming electrodes for detecting electrical characteristics of the gas sensitive material and detecting electrical characteristics of the insulative layer, the processor utilizing the detected electrical characteristics of the gas sensitive material, the detected electrical characteristics of the insulative layer and data from the temperature sensor to determine a gas concentration.

21. The gas sensor of claim 20, the detected electrical characteristics of the gas sensitive material being a resistance characteristic and the detected electrical characteristic of the insulative layer being a capacitive characteristic.

* * * * *